United States Patent
Huang et al.

(10) Patent No.: US 7,442,166 B2
(45) Date of Patent: Oct. 28, 2008

(54) DISPOSABLE TWO-STEP ENDOSCOPE

(75) Inventors: Ker-Jer Huang, Longtan Township, Taoyuan County (TW); Der-Ren Kang, Taipei (TW); Ping-Kuo Weng, Longtan Township, Taoyuan County (TW); Wei-Wu Kuo, Hsinchu (TW); Hsien-Ming Wu, Longtan Township, Taoyuan County (TW)

(73) Assignee: Chung Shan Institute of Science and Technology, Taoyuan County (TW)

( * ) Notice: Subject to any disclaimer, the term of this patent is extended or adjusted under 35 U.S.C. 154(b) by 434 days.

(21) Appl. No.: 11/125,124

(22) Filed: May 10, 2005

(65) Prior Publication Data

US 2006/0189846 A1  Aug. 24, 2006

(30) Foreign Application Priority Data

Feb. 23, 2005  (TW) ................................ 94105420 A

(51) Int. Cl.
*A61B 1/06* (2006.01)
*A61B 1/00* (2006.01)
(52) U.S. Cl. .................. 600/160; 600/114; 600/593
(58) Field of Classification Search .................. 600/109, 600/110, 114, 116, 160, 593
See application file for complete search history.

(56) References Cited

U.S. PATENT DOCUMENTS

| | | | |
|---|---|---|---|
| 5,604,531 A | 2/1997 | Iddan et al. | |
| 5,819,736 A * | 10/1998 | Avny et al. | 600/407 |
| 5,984,860 A * | 11/1999 | Shan | 600/116 |
| 6,240,312 B1 * | 5/2001 | Alfano et al. | 600/476 |
| 7,001,329 B2 * | 2/2006 | Kobayashi et al. | 600/114 |
| 2002/0103417 A1 * | 8/2002 | Gazdzinski | 600/109 |
| 2002/0198439 A1 | 12/2002 | Mizuno | |
| 2003/0158503 A1 | 8/2003 | Matsumoto | |
| 2004/0054278 A1 * | 3/2004 | Kimchy et al. | 600/407 |
| 2004/0133076 A1 * | 7/2004 | Kobayashi et al. | 600/175 |
| 2004/0138526 A1 * | 7/2004 | Guenst | 600/114 |
| 2004/0176664 A1 * | 9/2004 | Iddan | 600/160 |
| 2004/0215059 A1 | 10/2004 | Homan et al. | |
| 2005/0054902 A1 | 3/2005 | Konno | |
| 2005/0079132 A1 * | 4/2005 | Wang et al. | 424/1.11 |

FOREIGN PATENT DOCUMENTS

WO  WO 2004/054430  7/2004

OTHER PUBLICATIONS

H. J. Park et al., *Design of Bi-Directional and Multi-Channel Miniaturized Telemetry Module for Wireless Endoscopy*, 2nd Annual International IEEE-EMBS Special Topic Conference on Microtechnologies in Medicine & Biology May 2-4, 2002, pp. 273-276.

* cited by examiner

*Primary Examiner*—Henry M Johnson, III
*Assistant Examiner*—Victoria W Chen
(74) *Attorney, Agent, or Firm*—Rabin & Berdo, P.C.

(57) ABSTRACT

A disposable two-step endoscope for examining human organs includes an image capturing and transmission device and a cable that may be disconnected. The image capturing and transmission device includes a body, luminous devices, an optical image capturing device, a wireless transmission device and an internal power supply. The cable transmits the electric power outside and signals. The luminous device projects light on the human organs. The optical image capturing device captures organ images. The wireless transmission device transmits the organ images outside the human body. The internal power supply provides electric power for signal transmission after the cable and the image capturing and transmission device are separated.

12 Claims, 5 Drawing Sheets

DISPOSABLE TWO-STEP ENDOSCOPE

FIELD OF THE INVENTION

The invention relates to an endoscope system, and particularly to a disposable two-step endoscope to capture images for medical purposes of a patient's throat, stomach and small intestine in one examination.

BACKGROUND OF THE INVENTION

The endoscope is widely used to examine images of organs or perform surgical operations in a small area. The conventional endoscope usually employs an optical fiber system to capture tissue images by penetrating deeply into hollow organs of a human body (such as the stomach, large intestine and throat) to facilitate determination of the sources and developing conditions of illness. Light is transmitted through an optical fiber cable from a light source to project on the organ tissue. Images are transmitted back through the optical fiber cable to form images on an image sensor. The images are processed by a circuit and displayed on a screen. The optical fiber cable has to include many optical fibers to generate enough pixels. Such an optical fiber endoscope is expensive and complex. Fabrication is difficult, and maintenance is not easy. As the optical fiber endoscope is expensive, it has to be used repeatedly. Infection of patients is prone to occur if sterilization is not done properly. The disposable requirement is the tendency in the future.

Another problem of the optical fiber endoscope is that the flexible hose is too large and often inflicts pain upon the patient. Hence many patients are reluctant to undergo a stomach examination that involves the endoscope. Moreover, the present optical fiber endoscope for the digestive track can examine only the throat, stomach and large intestines. For the small intestines, which have a total length of six meters, the optical fiber endoscope can reach only the first ninety centimeters. Hence most of the small intestines cannot be examined.

In order to resolve the problem of examining the small intestines, referring to FIG. 1, Given image corporation (an Israeli company) has developed a vivo video camera system disclosed in U.S. Pat. No. 5,604,531. It can transmit image data by wireless to facilitate examination of the inner wall of the small intestines.

It is a wireless capsule endoscope 10 including a transparent optical front cover 12 and an opaque capsule shell 13 that are compatible with the human body. After being swallowed by a patient, the digestive tract 11 of the patient is adjacent to the transparent optical front cover 12. A light emitting diode (LED) 14 in the endoscope emits light to pass through the transparent optical front cover 12 and project on the inner wall of the digestive tract 11. Images are transmitted back through the transparent optical front cover 12, an image forming front lens 17a and an image forming rear lens 17b to form the images on a charge-coupled device (CCD) 16. A CCD actuator 15 drives the CCD 16 and sends the image signals to a wireless transmitter 18 for transmission. An antenna is located outside the patient to capture the image signals and send the signals to a reception system. After being processed by a circuit, the images are stored or displayed on a display device to be interpreted by doctors. A power supply module 19 is included to provide electric power for the operation of the entire capsule endoscope.

The wireless capsule endoscope is very helpful for examining the small intestines. However, the direction of the capsule endoscope cannot be controlled. Hence it is not suitable to examine the throat and stomach. As the number of patients suffering from illnesses in the small intestines is less than those suffering from the stomach illness, application of the capsule endoscope are limited.

SUMMARY OF THE INVENTION

In view of the aforesaid problems, the primary object of the invention is to provide a disposable two-step endoscope that can examine medical image of a patient's throat, stomach and small intestines at once to overcome the disadvantages of the conventional techniques, and offer a great benefit to patients who suffer from illnesses of digestive tract.

The disposable two-step endoscope according to the invention aims to examine human organs. It includes an image capturing and transmission device and a cable. The image capturing and transmission device includes a body, luminous devices, an optical image capturing device, a wireless transmission device and an internal power supply. The luminous devices are located on the front end of the body to provide light source. The optical image capturing device is located behind the luminous devices to convert the object image to electric signals. The wireless transmission device has a circuit connecting to the optical image capturing device to transmit the electric signals of the organs outside the human body. The internal power supply is connected to the rest of the devices to provide electric power while the body leaves the cable. The cable adopts a disconnection structure and is connected to a tail end of the image capturing.

In addition, when the disposable two-step endoscope of the invention is used in examining a patient's digestive tract. In the first step, to examine throat and stomach, transmission of the electric signals of the images and electric power are performed through a cable wired. Hence the image data can be displayed in a greater brightness and at a higher speed. Then in the second step, the disposable two-step endoscope is disconnecting, the electric signals of the images are transmitted by wireless when the body goes through to small intestines.

The foregoing, as well as additional objects, features and advantages of the invention will be more readily apparent from the following detailed description, which proceeds with reference to the accompanying drawings.

DESCRIPTION OF THE PREFERRED EMBODIMENTS

Figure 1:
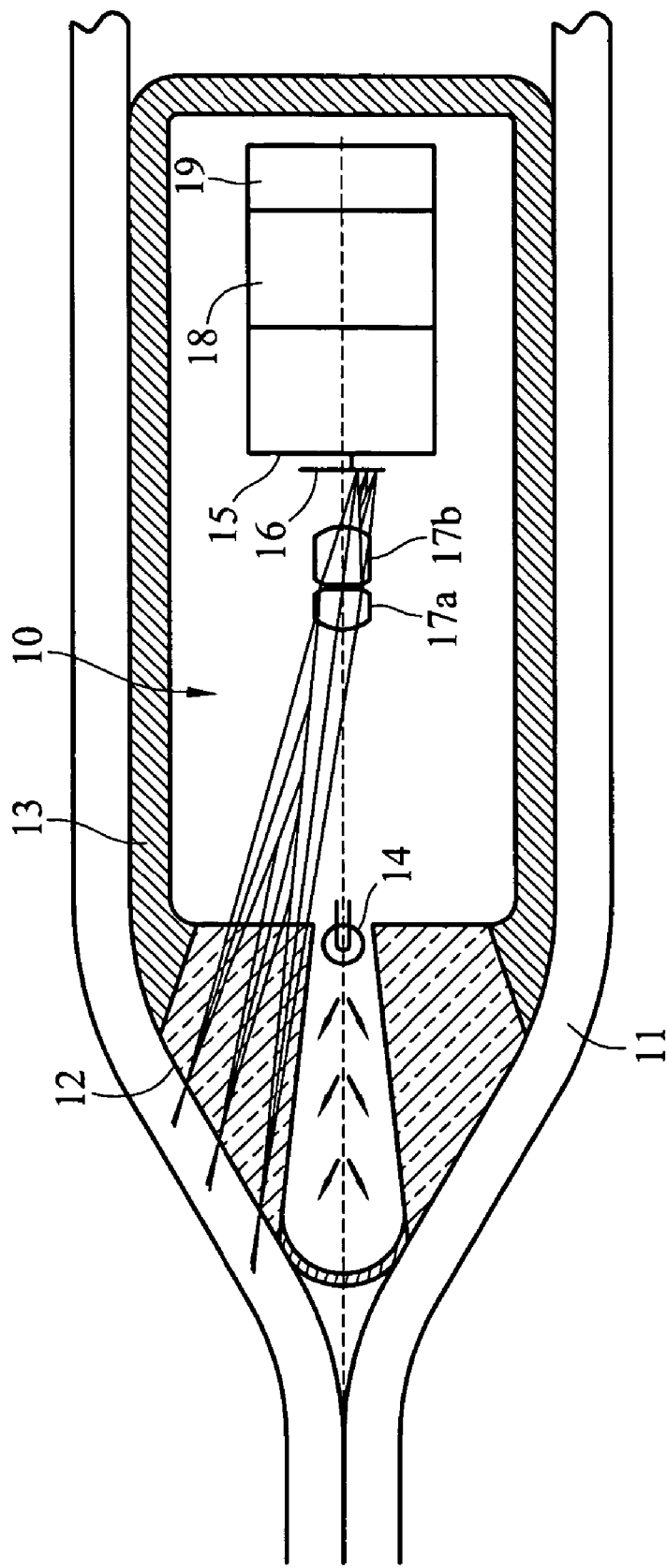
FIG. 1 is a schematic view of a conventional capsule endoscope.
Figure 2:
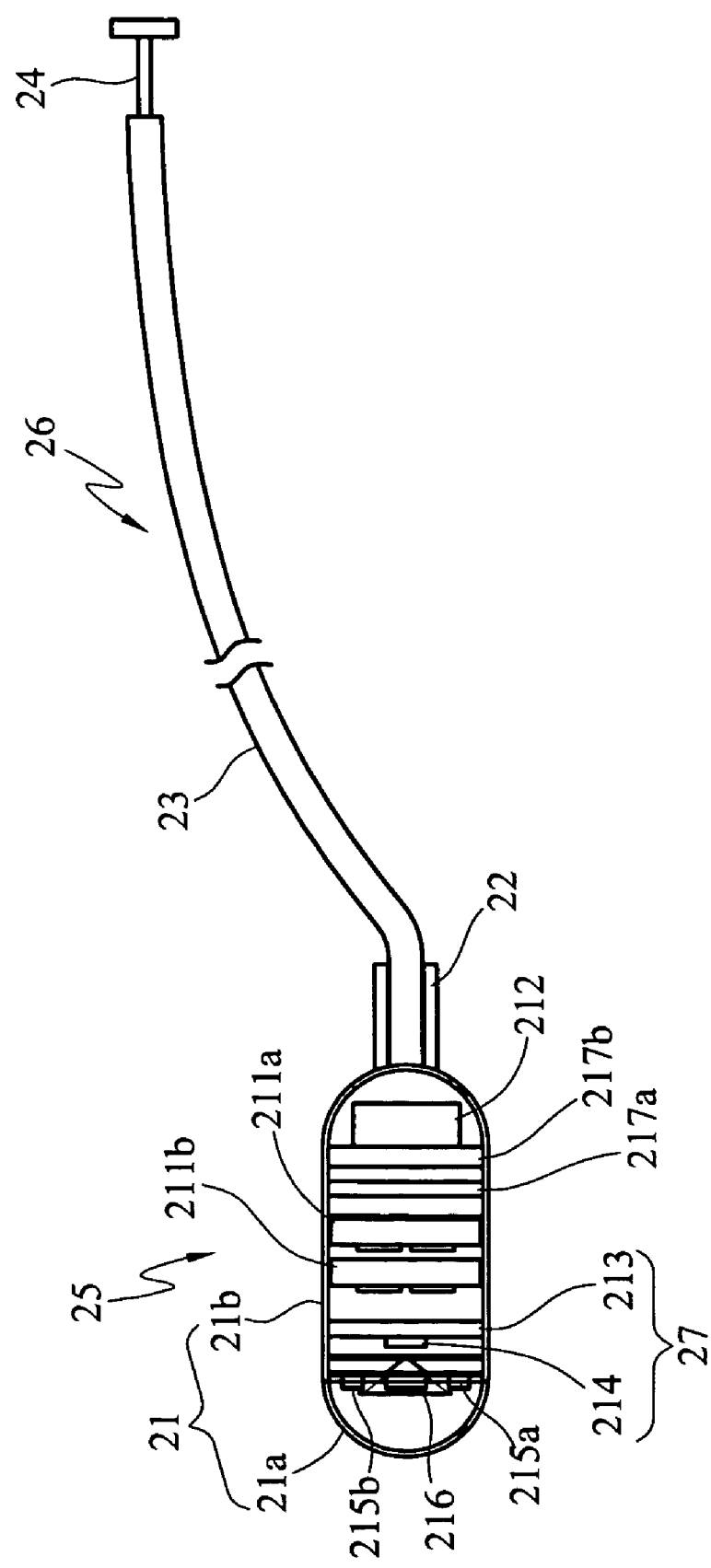
FIG. 2 is a schematic view of an embodiment of the disposable two-step endoscope of the invention.

Referring to FIG. 2, the disposable two-step endoscope according to the invention includes an image capturing and transmission device 25 and a cable 26. The image capturing and transmission device 25 includes a body 21, luminous devices 215a and 215b, an optical image capturing device 27, a wireless transmission device 212 and internal power supplies 211a and 211b. The body 21 is made from plastics compatible with the human body, and includes a transparent front window 21a and a shell 21b. The shell 21b has a diameter smaller than 11 mm. The optical image capturing device 27 is located in the front of the image capturing and transmission device 25. In this embodiment, the luminous devices 215a and 215b are light emitting diodes (LED). The optical image capturing device 27 includes a complementary metal oxide semiconductor (CMOS) image sensor 214 and an actuation circuit board 213. In front of the image sensor 214, there are the luminous devices 215a and 215b, and an image forming lens assembly 216. Light is emitted from the luminous devices 215a and 215b, passes through the transparent front window 21a, and projects on organs of a human body (such as the throat, stomach and intestines). Images are reflected through the transparent front window 21a and the image forming lens assembly 216 to form images on the image sensor 214. The image sensor 214 converts the object image to electric signals through the actuation circuit board 213. The electric signals may be transmitted through two ways. One way, a wired power supply and signal transmission means is used, with the electric signals being transmitted through circuit boards 217a and 217b, a disconnection mechanism 22 and a flexible hose 23 to an external circuit (not shown in the drawing) to be processed and stored or displayed on a display device. This approach is employed when the disposable two-step endoscope is used to examine the throat and stomach of the human body. The other way, a wireless transmission is adopted when the two-step endoscope is used to examine the intestines of the human body. The electric signals are sent to the wireless transmission device 212 (such as an antenna) for transmission. The wireless signals pass through the human body, are received by another antenna of a receiver outside the body, and are processed and stored in the receiver or displayed on a display device.

The internal power supplies 211a and 211b (such as batteries) located in the image capturing and transmission device 25 provide electric power to the luminous devices 215a and 215b, image sensor 214, wireless transmission device 212 and circuits when the disposable two-step endoscope is used to examine the intestines of the human body and is disconnected from the cable of power supply 21. As the internal power supplies 211a and 211b are used only when the image capturing and transmission device 25 is separated from the cable, electric power requirements are less than the wireless capsule endoscope 10, hence the sizes may be made smaller to make swallowing by the patient easier.

The cable 26 adopts a disconnection structure, and may be severed by a mechanical force or magnetic force. In this embodiment, the cable 26 includes the disconnection mechanism 22, the flexible hose 23 compatible with the human body and a pushbutton 24. It is connected to the image capturing and transmission device 25 through the disconnection mechanism 22. At the first step, the two-step endoscope is used to examine the human throat and stomach, and is controlled through a wire. The power cord and signal line are connected to the circuit of the image capturing and transmission device 25 through the flexible hose 23 and the disconnection mechanism 22.

Figure 3A:
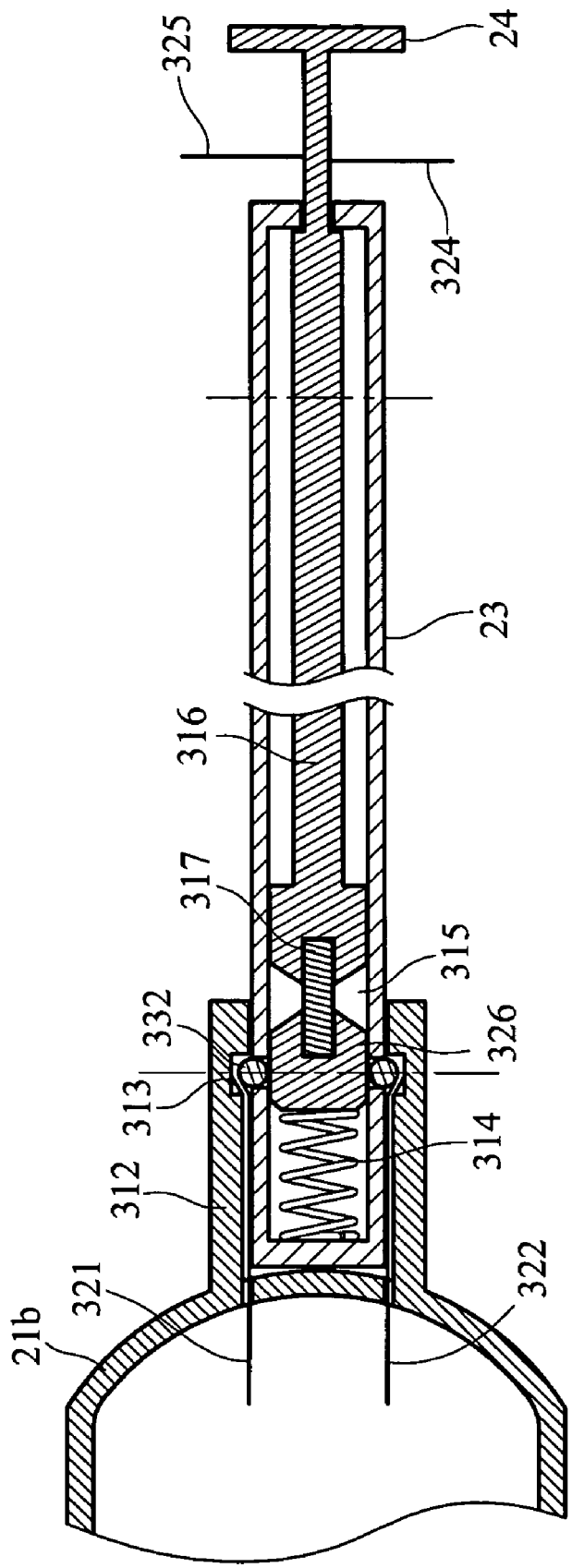
FIG. 3A is a schematic view of an embodiment of the disconnection mechanism of the invention.

Refer to FIG. 3A for an enlarged sectional view of the cable 26 (not shown in a proportional relationship). The flexible hose 23 contains the disconnection mechanism and is coupled with a disconnection shell 312 extended from the shell 21b on the tail end of the image capturing and transmission device 25. The disconnection mechanism includes a steel ball 332 extending out from the outer surface of the flexible hose, 23 to ram a leaf spring 313 into a steel ball trough formed on the disconnection shell 312 so that the flexible hose 23 and the disconnection shell 312 can be coupled together without loosening. The steel ball 332 is coupled tightly with the leaf spring 313. The leaf spring 313 is also connected to signal lines 321 and 322 located in the image capturing and transmission device 25. The steel ball 332 is further connected to other signals lines 324 and 325 located in the flexible hose 23 to connect to external circuits so that electric power outside can be transmitted to the image capturing and transmission device 25 for operation use. The image data obtained by the image capturing and transmission device 25 can be sent out for storing or displaying outside through the cable 26.

Figure 3C:
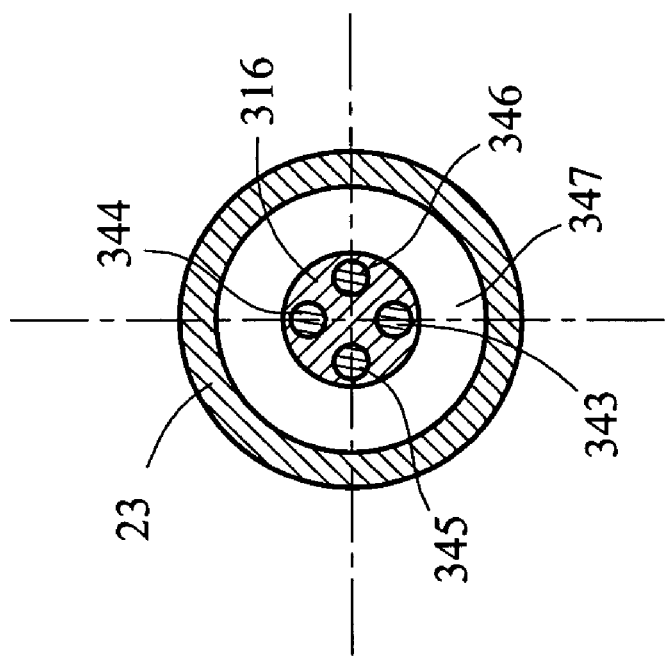
FIG. 3C is a schematic view of a cross section of the flexible hose of an embodiment of the disconnection mechanism of the invention.
Figure 3B:
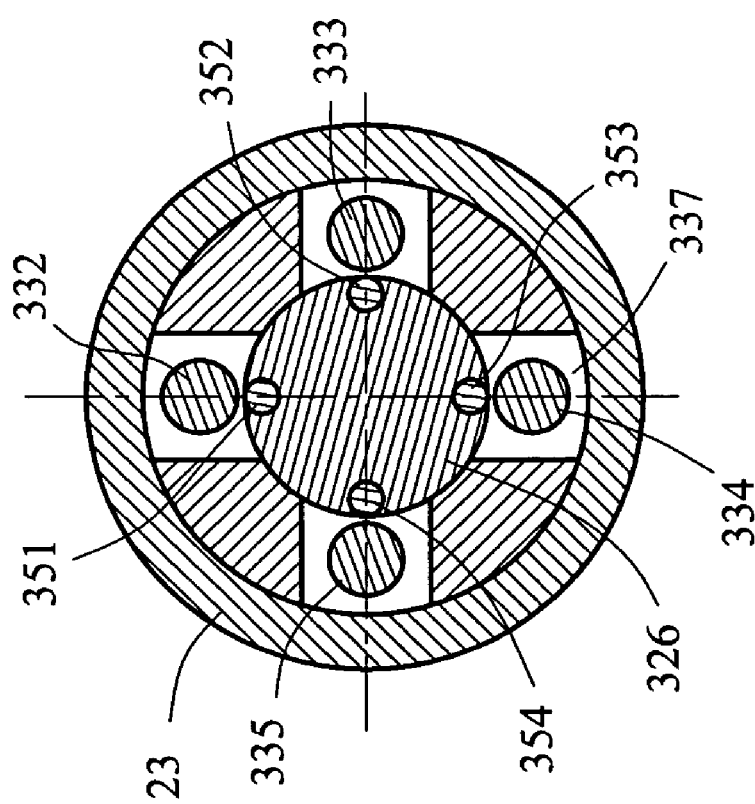
FIG. 3B is a schematic view of a cross section of the steel ball of an embodiment of the disconnection mechanism of the invention.

Refer to FIG. 3B for a cross section of the cable 26 of FIG. 3A where the steel ball 332 is located. Steel balls 332 and 334 are connected to power cords 351 and 353, and steel balls 333 and 335 are connected to signal lines 352 and 354. The power cords 351 and 353 and the signal lines 352 and 354 are embedded in an axle 316 made from a tough plastic. The steel ball 334 is located in a steel ball trough 337. All elements are encased in the disconnection shell 312.

Refer to FIG. 3C for a cross section of the flexible hose 23. Power cords 344 and 343, and signal lines 345 and 346 are embedded in the axle 316 that is surrounded by a gap 347 and is then encased by the flexible hose 23. When the disposable two-step endoscope is operated in the first step to examine the throat or stomach of the human body, the required electric power of all elements is supplied externally through the cable 26 in the flexible hose 23, including the luminous devices 215a and 215b, CMOS image sensor 214, wireless transmitter and circuits.

By means of the approach set forth, there is no limitation of power supply. Hence a light source of a greater brightness may be provided. Moreover, image signals are transmitted through the cable. Image quality and picture frame number per second can match those achieved by the conventional stomach endoscope. As the image signals are transmitted through a plurality of electric wires, and the hose is pliable, the cable can be made smaller than the optical fiber cable of the conventional endoscope. Moreover, since the cable is flexible, it can be bent to a smaller curvature radius. By contrast, the optical fiber cable of the conventional endoscope does not have a desired flexibility, and has to be bent at a greater curvature radius, hence is more difficult to use.

After examining the stomach with the disposable two-step endoscope, the second step start, the doctor can depress the pushbutton 24 to push the axle 316. The axle 316 moves a ramming member 326 forwards to compress a spring 314. The steel ball 332 is attracted by a strong magnet 317 into another steel ball trough 315 without latching the disconnection shell 312. Then the flexible hose 23 may be separated from the disconnection shell 312.

Figure 4:
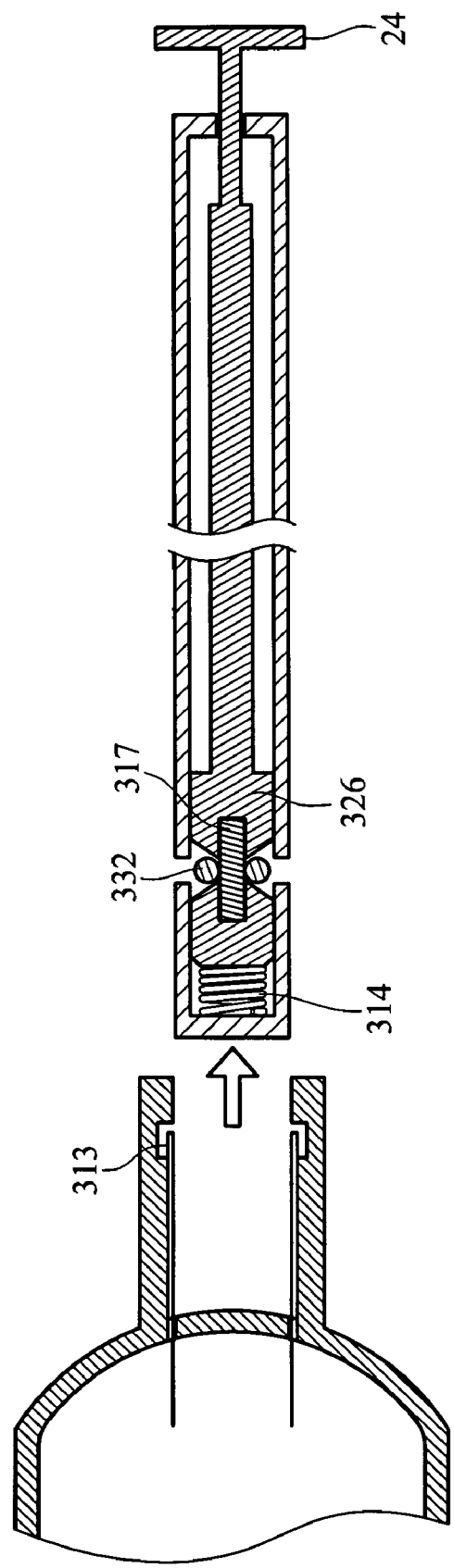
FIG. 4 is a schematic view of a cross section of the flexible hose of the invention after being disconnected.

Refer to FIG. 4 for a condition in which the flexible hose 23 is separated from the image capturing and transmission device 25. The pushbutton 24 is depressed, the axle 316 and the ramming member 336 are moved forward, the spring 314 is compressed, the leaf spring 313 is straightened again, and the steel ball 332 is attracted by the strong magnet 317 and disengaged. Hence the image capturing and transmission device 25 can enter the intestines smoothly. In the image capturing and transmission device 25, there is an information switch. When the steel ball 332 is loosened, the internal power supplies 211a and 211b in the image capturing and transmission device 25 are activated to provide electric power to the image capturing and transmission device 25. The image capturing and transmission device 25 functions as a general wireless capsule endoscope. Hence the two-step capsule endoscope has more advantages than the optical fiber stomach endoscope and the wireless capsule endoscope, and can perform a complete examination of the digestive system.

While the preferred embodiments of the invention have been set forth for the purpose of disclosure, modifications of the disclosed embodiments of the invention as well as other embodiments thereof may occur to those skilled in the art. Accordingly, the appended claims are intended to cover all embodiments which do not depart from the spirit and scope of the invention.

What is claimed is:

1. A disposable two-step endoscope for examining organs of a human body, comprising:
    an image capturing and transmission device, including:
        a body;
        a luminous device located in the body to provide a light signal adapted to illuminate the organs of the human body;
        an optical image capturing device located behind the luminous device to convert the light signal to an electric signal;
        a wireless transmitter having a circuit connecting to the optical image capturing device to transmit the electric signal outside the human body; and
        an internal power supply located in the body having another circuit connecting to the body, the luminous device, the optical image capturing device, and the wireless transmitter to provide electric power required; and
    a cable connecting to a tail end of the image capturing and transmission device to channel an external power supply and transmit the electric signal, and having a disconnection mechanism which is coupled with the image capturing and transmission device to control connection and disconnection between the cable and the image capturing and transmission device, the disconnection mechanism including a steel ball trough and a leaf spring, the leaf spring having one end fastened to one side of the steel ball trough, the cable further having a flexible hose which is made from a material compatible to the human body and being coupled with a rear end of the disconnection mechanism, the flexible hose including a steel ball, the flexible hose being latched in the steel ball trough by pressing the steel ball on the leaf spring, the leaf spring being connected electrically to the image capturing and transmission device through the flexible hose.

2. The disposable two-step endoscope of claim 1, wherein the body has a transparent front window and a shell, the transparent front window being located in front of the shell for housing the luminous device.

3. The disposable two-step endoscope of claim 1, wherein the body is made from a material compatible to the human body.

4. The disposable two-step endoscope of claim 1, wherein the cable includes two or more power cords and two or more signal lines to transmit respectively electric power and the electric signals.

5. The disposable two-step endoscope of claim 1, wherein the cable further includes a pushbutton adapted to be controlled by human hands to loosen or fasten the disconnection mechanism.

6. The disposable two-step endoscope of claim 5, wherein the cable further includes an axle which is connected to the pushbutton and movable by the pushbutton to move the steel ball away from the steel ball trough to disconnect the flexible hose from the image capturing and transmission device.

7. The disposable two-step endoscope of claim 1, wherein the cable is separated from the image capturing and transmission device by a mechanical force or magnetic force.

8. The disposable two-step endoscope of claim 1, wherein a shell of the image capturing and transmission device has a diameter smaller than 11 millimeters.

9. The disposable two-step endoscope of claim 1, wherein the luminous device is a light emitting diode.

10. The disposable two-step endoscope of claim 1, wherein the optical image capturing device includes an image sensor to receive the light signal and an actuation circuit board to convert the light signal to the electric signal.

11. The disposable two-step endoscope of claim 10, wherein the image sensor is a complementary metal oxide semiconductor (CMOS) image sensor.

12. A disposable two-step endoscope for examining organs of a human body, comprising:
    an image capturing and transmission device, including:
        a body;
        a luminous device located in the body to provide light that projects on the organs of the human body;
        an optical image capturing device located behind the luminous device to convert light reflected off the organs to an electric signal;
        a wireless transmitter having a circuit connected to the optical image capturing device to transmit the electric signal outside the human body;
        an internal power supply located in the body having another circuit connected to the body, the luminous device, the optical image capturing device, and the wireless transmitter to provide electric power;
        a disconnection shell attached to a rear of the body, the disconnection shell having a steel ball trough formed therein; and
        a leaf spring electrically connected to at least the luminous device and the optical image capturing device, the leaf spring being engageable with the steel ball trough;
    a cable removably connected to the disconnection shell to channel an external power supply and transmit the electric signal via the leaf spring, and having a disconnection mechanism which is coupled with the disconnection shell to control connection and disconnection between the cable and the image capturing and transmission device, the cable further having a flexible hose which is made from a material compatible to the human body, the flexible hose having the disconnection mechanism disposed therein, the disconnection mechanism including a steel ball, the flexible hose being latched to the disconnection shell by pressing the steel ball against the leaf spring and into the steel ball trough, the image capturing and transmission device being electrically connected to at least the external power supply via the leaf spring and the flexible hose.

* * * * *